United States Patent [19]

Belenduik et al.

[11] Patent Number: 5,447,729
[45] Date of Patent: Sep. 5, 1995

[54] MULTILAMELLAR DRUG DELIVERY SYSTEMS

[75] Inventors: George W. Belenduik, Potomac; Edward M. Rudnic, No. Potomac, both of Md.; John A. McCarty, Biscayne Park, Fla.

[73] Assignee: PharmaVene, Inc., Gaithersburg, Md.

[21] Appl. No.: 224,340

[22] Filed: Apr. 7, 1994

[51] Int. Cl.⁶ .................................................. A61K 9/16
[52] U.S. Cl. .................................... 424/490; 424/476; 424/489; 424/469; 424/463
[58] Field of Search ................ 424/489, 490, 472, 469

[56] References Cited

U.S. PATENT DOCUMENTS

| | | | |
|---|---|---|---|
| 4,963,365 | 10/1990 | Samejima et al. | 424/462 |
| 5,202,128 | 4/1993 | Morella et al. | 424/469 |
| 5,350,741 | 9/1994 | Takada | 424/472 |

Primary Examiner—Thurman K. Page
Assistant Examiner—William E. Benston, Jr.
Attorney, Agent, or Firm—Charles J. Herron; Elliot M. Olstein

[57] ABSTRACT

A pharmaceutical preparation including a pharmaceutical agent incorporated into particles comprising (i) a core formed from a hydrophilic material, a hydrophobic material or a hydrophobic emulsion or dispersion and (ii) an alternating sequence of hydrophilic/hydrophobic layers thereon such that there is a hydrophilic/hydrophobic interface between the core and each succeeding layer.

21 Claims, No Drawings

MULTILAMELLAR DRUG DELIVERY SYSTEMS

The ability of drugs to be administered via the oral route depends on several factors. The drug must be soluble in the gastrointestinal fluids in order for the drug to be transported across biological membranes, or be suitable for an active transport mechanism. Very small particulates (less than 300 nanometers) can be absorbed through the Peyer's Patch system in the small intestine, and through the lymphatic system, but this mechanism is not capable of absorbing large doses of drugs into the systemic circulation.

A problem arises for hard to dissolve drugs. In the case of conventional drugs, some drugs are relatively insoluble in gastrointestinal fluids. If the extent of solubility is low, this may cause incomplete and/or erratic absorption. If the rate of solubility is low, then absorption will most probably be erratic on an intra-patient and inter-patient basis. Peptide drugs can be water soluble, and these are not as problematic as insoluble peptides. Like conventional drugs, insoluble peptides typically exhibit incomplete or low extent of absorption and erratic absorption or bioavailability.

The primary issue in the ability to deliver peptides orally is the protection of the drug from proteolytic enzymes. There are two basic approaches to do this. The first is an "enteric" coating that can be applied to release the drug only in neutral to basic pH, so that the peptide is not exposed to gastric juices. However, this approach alone is not sufficient to protect the peptide since proteolytic enzymes exist in the upper intestinal tract, and some degradation of the drug can still occur. The other approach is to incorporate the peptide in a hydrophobic material so that aqueous fluids cannot penetrate the system. In this way, the peptide is protected from proteolytic enzymes. In addition, it is possible to combine the two approaches.

However, there are inherent difficulties with the approach outlined above. First, many drugs are released too slowly from hydrophobic systems. Also, some peptides will partition into the hydrophobic phase so that they will not be fully released from these systems. Thus, both the rate and extent of drug release are crucial components of any drug delivery system, and are even more important for many peptide drugs.

In accordance with the present invention there is provided a pharmaceutical preparation or delivery system including a pharmaceutical agent incorporated into particles comprising (i) a core formed from a hydrophilic material, a hydrophobic material or a hydrophobic emulsion or dispersion and (ii) an alternating sequence of hydrophilic/hydrophobic layers thereon such that there is a hydrophilic/hydrophobic interface between the core and each succeeding layer.

The particles include the core or prill seed and multiple alternating hydrophobic and hydrophilic layers, forming solid-state or semi-solid vesicles, in a multilamellar structure. The core can be formed of hydrophilic or hydrophobic materials or of a hydrophobic discontinuous phase emulsified or dispersed in a hydrophilic continuous phase, in which case the surface of the core or seed will take on the hydrophilic character of the continuous phase. The surfactant and the two phases stabilized form an emulsion. This emulsion can take the form of a complex water-in-oil-in-water-etc. emulsion oil-in-water-in-oil-etc. emulsion. Each phase can be very small in size or volume, or can be a discernible coating over the previous phase with a surfactant stabilizing the interface. Hydrophilic and hydrophobic layers are formed onto the core or seed such that there is always an alternating hydrophilic/hydrophobic interface formed. Thus, a core with a hydrophilic surface will first be coated with a hydrophobic layer followed by a hydrophilic layer, and vice versa.

Drugs of the type delivered by the delivery system of the invention partition into either or both phases, according to the drugs' partition coefficient and are released from the particles by diffusion and erosion of the vesicle in vivo. The spheres can be delivered by the oral, nasal, otic or inhalation routes of administration and have a size range of from 0.5 to about 100 microns.

When the core is formed of an emusion the hydrophobic material forms the discontinuous phase and the hydrophilic material forms the continuous phase in which the hydrophobic material is emulsified. The hydrophobic discontinuous phase and the hydrophilic continuous phase can each independently be solid, semi-solid or liquid. The pharmaceutical agent may be dispersed or incorporated into the hydrophobic material, the hydrophilic material or in both the hydrophobic and hydrophilic materials. Preferably the carrier emulsion is a colloid, microcolloidal emulsion or, most preferably, a microemulsion.

An emulsion is a disperse system containing at least two immiscible phases, a hydrophobic phase and a hydrophilic phase. The emulsion comprises the dispersed phase, the dispersion phase and an emulsifying agent or surfactant agent, except when the hydrophobic material is a "self-emulsifying" ester, making a separate emulsifying agent unnecessary. The term "colloidal" refers to emulsions in which the dispersed phase is of very fine particles, usually less than about 1 mm in size. A "microcolloid" is an emulsion wherein the dispersed particles are usually about 100 um or less in size. Cosurfactants are also common components of microcolloids and are simply surfactants included in addition to the primary surfactant. A "microemulsion" is an optically isotropic and thermodynamically stable liquid emulsions.

The emulsions of the invention are generally made by adding hot (70°–80° C.) hydrophobic phase (smaller by weight) to hot (70°–80° C.) hydrophilic phase (larger by weight) forcing inversion of the surface active agent to form a disperse emulsion of unaggregated dispersed phase particles. This produces an emulsion when processed under suitable shear. The drug is usually added with the hydrophobic material when it is an organic molecule that is poorly soluble in aqueous media. The drug is usually added after the emulsion has been formed and allowed to cool when it is a peptide. The drug in emulsion formulation is then filled into a soft or hard gelatin capsule, tablet or other oral dosage form.

In the multilamellar pharmaceutical preparation of the present invention certain hydrophobic materials provide enhanced absorption capabilities for oral delivery of peptide drugs and drugs that are poorly soluble in aqueous media. In accordance with the invention, these materials are preferably selected from the group consisting of long chain carboxylic acids, long chain carboxylic acid esters, long chain carboxylic acid alcohols and mixtures thereof. Certain long chain carboxylic acid esters are self-emulsifying, that is that a surfactant is not necessary for these compounds to be emulsified into a hydrophilic phase.

The long chain carboxylic acids, generally contain from 6–30 carbon atoms and preferably contains at least 12 carbon atoms, most preferably 12 to 22. In some cases this carbon chain is fully saturated and unbranched, while others contain one or more double bonds. A few contain 3-carbon rings or hydroxyl groups. Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocaboxyic acids. Examples of these are linoleic acid, linolenic acid, arachidonic acid and behenolic acid. Useful branched acids include, for example, diacetyl tartaric acid.

Examples of long chain carboxylic acid esters include, but are not limited to, those from the group of: glyceryl monostearates; glyceryl monopalmitates; mixtures of glyceryl monostearate and glyceryl monopalmitate (Myvaplex 600, Eastman Fine Chemical Company); glyceryl monolinoleate; glyceryl monooleate; mixtures of glyceryl monopalmitate, glyceryl monostearate glyceryl monooleate and glyceryl monolinoleate (Myverol 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (Myverol 18-99, Eastman Fine Chemical Company); acetylated glycerides such as distilled acetylated monoglycerides (Myvacet 5-07, 7-07 and 9-45, Eastman Fine Chemical Company); mixtures of propylene glycol monoesters, distilled monoglycerides, sodium stearoyl lactylate and silicon dioxide (Myvatex TL, Eastman Fine Chemical Company); mixtures of propylene glycol monoesters, distilled monoglycerides, sodium stearoyl lactylate and silicon dioxide (Myvatex TL, Eastman Fine Chemical Company) d-alpha tocopherol polyethylene glycol 1000 succinate (Vitamin E TPGS, Eastman Chemical Company); mixtures of mono- and di-glyceride esters such as Atmul (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboyxlic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; cetearyl octanoate; $C_{10}$–$C_{30}$ cholesterol/lavosterol esters; and sucrose long chain carboxylic acid esters.

Examples of the self-emulsifying long chain carboxylic acid esters include those from the groups of stearates, palmitates, ricinoleates, oleates, behenates, ricinolenates, myristates, laurates, caprylates, and caproates.

The alcohols useful in the invention are exemplified by the hydroxyl forms of the carboxylic acids exemplified above and also cetearyl alcohol.

The types of protective or sustained release coatings that can be used include, but are not limited to, ethylcellulose, hydroxypropylmethylcellulose, hydroxypropylcellulose, hydroxyethylcellulose and esters of methacrylic and ethacrylic acid (Eudragit RL, RS, and NE polymer products, Rohm Pharma, Darmstadt, Germany). The enteric protective materials or coatings can be, for example, cellulose acetate pthalate, hydroxypropylmethylcellulose pthalate, ethylvinylacetate pthalate, polyvinylacetate pthalate and esters of methacrylic and ethacrylic acid (Eudragit S and Eudragit L, Rohm Pharma, Darmstadt, Ger.).

The composition or preparation of the invention can further include a surfactant, an amphiphilic molecule consisting of a hydrophobic tail and a hydrophilic head. These molecules possess distinct regions of both hydrophilic and hydrophobic character. The hydrophobic tai can be a hydrocarbon or fluorocarbon chain of 8 to 18 carbon atoms. The hydrophilic head can be ammonium, sulfate, sulfonate or carboxylate if ionic, and polyoxyethylene if non-ionic. They are long chain molecules such as, for example, soaps or detergents. Surfactants accumulate at the hydrophilic/hydrophobic (water/oil) interface and lower the surface tension. Surface active agents or surfactant are long chain molecules, such as soaps and detergents, which accumulate at the hydrophilic/hydrophobic (water/oil) interface and lower the surface tension. One effect of a reduced surface tension is the stabilization of the emulsions. This is because molecules with both polar and non-polar groups become oriented such that the hydrocarbon tail embeds itself into the hydrophobic phase and the hydrophilic head protrudes into the hydrophilic phase. Where the hydrophobic composition or other component of the preparation includes a surface-active agent, such as a surfactant, it is usually present in amounts of about 0.05% to 10.0% weight/weight of the hydrophobic composition with a preferred range of 0.1% to 2.0% (w/w).

The drugs to be incorporated individually or as combinations in the pharmaceutical preparations of the invention are those having less than about 80% oral bioavailability. The term "bioavailability" as used here means the rate and extent of systemic absorption of a drug from the oral route of administration.

In one aspect, the drug is a polypeptide, usually of less than about 15 amino acids. Examples include cyclosporin, angiotensin I, II and III, enkephalins and their analogs, ACTH, antiinflammatory peptides I, II, III, bradykinin, calcitonin, cholecystikinin (CCK) fragments 26–33 and 30–33, pre/pro CCK (V-9-M), β-endorphin, dinorphin, leucokinin, leutinizing hormone releasing hormone (LHRH), neurokinins (e.g. neurokinin A), somatostatin, substance P, thyroid releasing hormone (TRH) and vasopressin.

In another aspect, the drug is an organic molecule that is poorly soluble in aqueous media. These organic molecules usually have a molecular weight (m.w.) of less than about 1,000 daltons, and usually less than about 600 daltons. Examples include acyclovir, adriamycin, cabamazepine, griseofulvin, angiotensin converting enzyme inhibitors, flutamide, melphalan, nifedipine, indomethacin, naproxen, estrogens, testosterones, steroids, phenytoin, sumatripan, ergotamines and cannabinoids.

In accordance with the invention, drugs are incorporated into hydrophobic materials by admixture using conventional mixing devices and homogenizers used for semi-solid ointments and lotions, with agitation at speeds common to emulsified products such as creams and emulsions. Examples of common equipment employed are propeller or turbine mixers, homogenizers, colloid mills, ultrasonic mixers and microfluidizers. The shear of the agitation should be sufficient to form a stable dispersion, but not too great to cause degradation of the drug. Suitable homogenizers are available from Micromedics, Inc., Silverson, APV Crepaco and Arde Barinco.

This hydrophobic emulsion or dispersion is then formed into particles by spray-congealing or "prilling." This process uses a spray nozzle which atomizes the material in a cooling tower. As the material is sprayed, surface tension causes a uniform spherical particle to be formed. As the particle falls through the cooling chamber, it hardens into a stable, intact sphere. These spheres can be sprayed in a variety of diameters, generally from 0.5 microns to 100 microns. It is preferred to reduce the size of the sphere as much as possible, preferably below 5 microns for the primary hydrophobic "seed" prill.

These particles are then coated in a fluidized bed apparatus with an alternating sequence of (i) a surfactant-containing hydrophilic solution and (ii) a stable emulsion or dispersion of the drug in a hydrophobic material to provide the multilamellar drug delivery system of the invention. The hydrophilic phase is sprayed on with a binder that adheres to the hydrophobic seed. Then a hydrophobic material is sprayed on which will adhere the aqueous surfactant phase. What follows is a process of repeatedly alternating between these two steps in a fluid bed apparatus. This is done in one fluid bed that has differential pressures that organize the flow in that bed. The seed is repeatedly coated with the hydrophilic solution for a set number of minutes and then with the hydrophobic emulsion or dispersion for an independent set number of minutes. The apparatus used is a fluid-bed coating apparatus, such as is available from Wurster and others.

The newly coated particles are then coated with the hydrophobic mixture from above, and then alternating hydrophilic and hydrophobic coatings to produce a multilamellar structure. The drug partitions into each phase, according to its partition coefficient, and is released from the system by diffusion, erosion, and enhanced dissolution resulting from the surface-active nature of the interfaces.

The particles can be incorporated into hard gelatin capsules, either with additional excipients, or alone. Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other material imparting flow to powders. Because of their hydrophobic nature, the particles should not need a lubricant, but one can be added if necessary by using polyethylene glycol, leucine, glyceryl behenate, magnesium stearate or calcium stearate.

The particles may also be incorporated into a tablet, in particular by incorporation into a tablet matrix, which rapidly disperses the particles after ingestion. In order to incorporate these particles into such a tablet, a filler/binder must be added to a tablet that can accept the particles, but will not allow their destruction during the tableting process. Materials that are suitable for this purpose include, but are not limited to, microcrystalline cellulose (Avicel), soy polysaccharide (Emcosoy), pregelatinized starches (STARCH 1500, National 1551), and polyethylene glycols (Carbowax). The materials should be present in the range of 5–75% (w/w), with a preferred range of 25–50% (w/w).

In addition, disintegrants are added in order to disperse the particles once the tablet is ingested. Suitable disintegrants include, but are not limited to: cross-linked sodium carboxymethyl cellulose (Ac-Di-Sol), sodium starch glycolate (Explotab, Primojel), and cross-linked polyvinylpolypyrrolidone (Plasdone-XL). These materials should be present in the range of 3–15% (w/w), with a preferred range of 5–10% (w/w).

Lubricants are also added to assure proper tableting, and these can include, but are not limited to: magnesium stearate, calcium stearate, stearic acid, polyethylene glycol, leucine, glyceryl behanate, and hydrogenated vegetable oil. These lubricants should be present in amounts from 0.1–10% (w/w), with a preferred range of 0.3–3.0% (w/w).

Tablets are formed, for example, as follows. The particles are introduced into a blender along with Avicel, disintegrants and lubricant, mixed for a set number of minutes to provide a homogeneous blend which is then put in the hopper of a tablet press with which tablets are compressed. The compression force used is adequate to form a tablet; however, not sufficient to fracture the beads or coatings.

The capsule or tablet can also be enteric coated. Either the particles can be enteric coated (Ph sensitive) and released in the stomach or the capsule or tablet can be enteric coated (thereby releasing the particles in the intestine), in which case the particles need not be so coated. To use only a sustained release coating on the particle one would also need an enteric coated capsule or tablet. There are three approaches here. First, there is the uncoated hydrophobic particle in an enteric coated capsule. Second, there is the sustained release coated particle within an enteric coated capsule or tablet. Third, there is the enteric coated particle enclosed within a regular soft gelatin capsule or uncoated tablet.

The capsule may be further processed to provide gastric protection by enterically coating the capsule. When the contents of the capsule are released into the gastrointestinal milieu, it spontaneously forms a microcolliodal emulsion with the gastrointestinal fluid. The gastrointestinal fluid acting as the aqueous phase.

The preparation of an emulsion based system, requires that the drug be dispered into the hydrophobic material as described above, with the aqueous phase being added in the presence of surfactant or self-emulsifying hydrophobic long chain carboxylic acid ester. This procedure under suitable shear forms a microemulsion. This emulsion is then filled into a soft of hard gelatin capsule. The capsule may be further processed to provide gastric protection by enterically coating the capsule.

EXAMPLE 1

| Phase | Ingredients | % W/W |
| --- | --- | --- |
| B | Somatostatin | 15 |
| B | Polyethylene Glycol 4000 | 20 |
| B | Polyethylene Glycol 8000 | 20 |
| A | Polysorbate 80 | 5 |
| A | Oleic Acid | 40 |

Preparation: To form the emulsion core, mix a portion of the ingredients of Phase A with Phase B at 70°–80° C., then cool in a spray-drying or "prilling" column to form beads. Then mix the beads in a portion of melted PEG 4000 and 8000, and add the drug, Polysorbate 80 and oleic acid to the mixture. Repeat this last step one to four times.

EXAMPLE 2

| Phase | Ingredients | % W/W |
|---|---|---|
| B | Cyclosporin | 25 |
| B | Glyceryl Monooleate | 15 |
| A | Peg-25 Glyceryl Trioleate | 10 |
| B | Ceteryth-20 | 5 |
| A | Oleyl Alcohol | 45 |
| A | Water | q.s. |

Preparation: The emulsion core is made by adding glyceryl monooleate, oleyl alcohol and ceteryth-20 in a heated vessel at >40° C. Add the cyclosporin. Mix the PEG-25 glyceryl trioleate in water at 40° C. Prill a portion of the phase B materials, and suspend them in a spray-drying apparatus. Alternate coats of phase A and phase B at least two times, and up to five times.

EXAMPLE 3

| Phase | Ingredients | % W/W |
|---|---|---|
| A | Calcitonin | 30 |
| B | Vitamin E TPGS | 10 |
| C | Medium Chain Mono and diglycerides | 15 |
| D | Polysorbate 80 | 5 |
| E | Hydroxypropylmethyl cellulose | 10 |
| F | Polyethylene Glycol 400 | 10 |
| G | Water | 20 |

Preparation: To form emulsion core, first melt Vitamin E TPGS thoroughly, to >40° C. Add a portion of the remaining ingredients to the melt. Heat water (G) to ~70°-80° C. then add mix of ingredients A through F. While mixing using a sutiable mixer, the cores can be made in a spray-drying or "prilling" column. Alternate layers can be applied using the ingredients in a fluidized-bed apparatus or suspending the prills in a portion of the PEG 400 and mixing in the rest of ingredients and "re-prilling" the mixture. Repeat this latter process up to five times.

What is claimed is:

1. A pharmaceutical preparation which comprises a pharmaceutical agent incorporated into particles having a diameter of about 0.5 to 100 microns comprising (i) a core comprising at least one member selected from the group consisting of a hydrophilic material and a hydrophobic material and (ii) at least first and second layers each comprising at least one member selected from the group consisting of hydrophilic material and hydrophobic material and wherein an interface between the core and the first layer and between adjacent layers is an interface between hydrophobic and hydrophilic material.

2. The pharmaceutical composition of claim 1 wherein the core has a diameter of less than about 5 microns.

3. The pharmaceutical preparation of claim 2 wherein the particles have a diameter of less than about 10 microns.

4. The pharmaceutical preparation of claim 1 wherein the emulsion or dispersion is selected from the group consisting of a colloidal emulsion, microcolloidal emulsion and a microemulsion.

5. The pharmaceutical preparation of claim 1 wherein the hydrophobic material is a long chain carboxylic acid having from 6 to 30 carbons and selected from the group consisting of n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid, melissic acid, oleic acid, gadoleic acid, erucic acid, tinoleic acid, linolenic acid, arachidonic acid, behenolic acid and diacetyl tartaric acid.

6. The pharmaceutical preparation of claim 1 wherein the hydrophobic material is a long chain carboxylic acid ester of a long chain carboxylic acid having from 6 to 30 carbons and is selected from the group consisting of glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearam glyceryl monooleate and glyceryl monolinoleate; glyceryl monolinolenate; glyceryl monogadoleate; mixtures of glyceryl monopaimitate, glyceryl monostearate, glyceryl monooleate, glyceryl monolinoleate, glyceryl monolinolenate and glyceryl monogadoleate; acetylated glycerides such as distilled acelyated monoglycerides; mixtures of propylene glycol monoesters, distilled monoglycerides, sodium stearoyl lactylate anal silicon dioxide; mixtures of propylene glycol monoesters, distilled monoglycerides, sodium stearoyl lactylate and silicon dioxide; d-alpha tocopherol polyethylene glycol 1000 succinate; mixtures of mono- and di-glyceride esters; calcium stearoyl lactylate; ethoxylated mono- and di-glycerides; lactated mono- and di-glycerides; lactylate carboxylic acid ester of glycerol and propylene glycol; lactylic esters of long chain carboxylic acids having from 6 to 30 carbons; polyglycerol esters of long chain carboxylic acids having from 6 to 30 carbons, propylene glycol mono- and di-esters of long chain earboxylic acids having from 6 to 30 carbons; sodium stearoyl iactylate; sorbitan monostearate; sorbitan monooleate; other sorbitan esters of long chain carboxylic acids having from 6 to 30 carbons; succinylated monoglycerides; stearyl monoglyceryl titrate; stearyl heptanoate; cetyl esters of waxes; stearyl octanoate; cholesterol/lavosterol esters; and sucrose esters of long chain carboxylic acids having from 6 to 30 carbons.

7. The pharmaceutical preparation of claim 1 wherein the hydrophobic material is a long chain carboxylic acid alcohol of a long chain carboxylic acid having from 6 to 30 carbons and is selected from the group consisting of n-dodecanoic acid alcohol, n-tetradccanoic acid alcohol, n-hexadccanoic acid alcohol, caproic acid alcohol, caprylic acid alcohol, capric acid alcohol, lauric acid alcohol, myristic acid alcohol, palmitic acid alcohol, stearic acid alcohol, arachidic acid alcohol, behenic acid alcohol, morttunic acid alcohol, melissic acid alcohol, oleic acid alcohol, gadoleic acid alcohol, crucic acid alcohol, behenolic acid alcohol and diacetyl tartaric acid alcohol.

8. The pharmaceutical preparation of claim 1 wherein the hydrophobic material of the emulsion is a self-emulsifying surface-active hydrophobic ester.

9. The pharmaceutical preparation of claim 8 wherein the self-emulsifying hydrophobic material is selected from the groups of stearates, palmitates, ricinoleates, oleates, behenates, ricinolenates, myristates, laurares, caprylates, and caproates.

10. The pharmaceutical composition of claim 1 which further comprises a surfactant that is present in a range of about 0.05 % to 10.0% weight/weight of the hydrophobic material.

11. The pharmaceutical preparation of claim 1 wherein the surfactant is present in a range of about 0.05% to 2.0% weight/weight of the hydrophobic composition.

12. The pharmaceutical preparation of claim 1 wherein the surfactant is selected from poloxamers, sodium lauryl sulfate, sorbitan fatty acid esters and sucrose esters of fatty acids.

13. The pharmaceutical preparation of claim 1 wherein the pharmaceutical agent has less than about 80% bioavailability.

14. The pharmaceutical preparation of claim 2 wherein the pharmaceutical agent is an organic molecule of less than about 1,000 daltons.

15. The pharmaceutical preparation of claim 14 wherein the organic molecule is less than about 600 daltons.

16. The pharmaceutical preparation of claim 1 wherein the pharmaceutical agent is selected from acyclovir, adriamycin, cabamazepine, griseofulvin, angiotensin converting enzyme inhibitors, flutamide, melphalan, nifedipine, indomethacin, naproxen, estrogens, testosterones, steroids, phenytoin, sumatripan, ergotamines and cannabinoids.

17. The pharmaceutical preparation of claim 1 wherein the emulsion is encapsulated in a capsule comprising an enteric coating material.

18. The pharmaceutical preparation of claim 4 wherein the microcolloidal emulsion is encapsulated in a capsule that is soluble in an acidic aqueous environment.

19. The pharmaceutical preparation of claim 1 wherein at least one of said layers is an emulsion.

20. The pharmaceutical preparation of claim 1 wherein said core comprises an emulsion of a hydrophobic material and a hydrophilic material as a water-in-oil emulsion.

21. The pharmaceutical preparation of claim 1 wherein said core comprises an emulsion of a hydrophilic material and a hydrophobic material as an oil-in-water emulsion.

* * * * *